United States Patent [19]
Gao et al.

[11] Patent Number: 6,110,425
[45] Date of Patent: Aug. 29, 2000

[54] BLOOD SMEAR SLIDE OUTLOADER

[75] Inventors: Daniel Dashui Gao, Dallas, Tex.; Thomas Wollitzer, North Miami Beach; Daniel B. Roberts, Miami, both of Fla.

[73] Assignee: Coulter International Corp., Miami, Fla.

[21] Appl. No.: 09/204,826

[22] Filed: Dec. 3, 1998

[51] Int. Cl.⁷ .................................................. G01N 35/00
[52] U.S. Cl. .............................. 422/66; 422/63; 422/65; 436/43; 436/44; 436/46
[58] Field of Search .................. 422/63, 65, 66, 422/104; 436/43, 44, 46

[56] References Cited

U.S. PATENT DOCUMENTS

| | | | |
|---|---|---|---|
| 4,269,803 | 5/1981 | Jessop | 422/63 |
| 5,049,359 | 9/1991 | Azuma et al. | 422/67 |
| 5,053,198 | 10/1991 | Quenin | 422/64 |
| 5,097,938 | 3/1992 | Gruner et al. | 198/397 |
| 5,356,595 | 10/1994 | Kanamon et al. | 422/65 |
| 5,766,549 | 6/1998 | Gao et al. | 422/65 |
| 5,871,696 | 5/1981 | Roberts et al. | 422/65 |

*Primary Examiner*—Long V. Le
*Attorney, Agent, or Firm*—Henry Hansen; Mitchell E. Alter

[57] ABSTRACT

A blood smear slide outloader including a platen for transferring a succession of slides from a dryer to a slide storage basket. The slides are sequentially discharged from one end of the dryer onto a platen and held firmly in place by a gripper. A single stepper motor then rotates the platen to a vertical position as it lowers both into alignment above a slot in the storage basket. A linear actuator causes the gripper to release the slide and deposit it into the slot. The platen then returns to the discharge end of the dryer to receive the next slide.

16 Claims, 7 Drawing Sheets

BLOOD SMEAR SLIDE OUTLOADER

BACKGROUND OF THE INVENTION

1. Field of The Invention

The present invention relates generally to improvements in apparatus for producing blood smears on glass microscope slides for laboratory analyses, and more particularly to an outloader for transferring blood smear slides from an automatic blood smear slide maker to a compartmented multi-slide storage basket.

2. Description of the Prior Art

Automatic blood smear slide making apparatus generally perform a sequence of operations for creating blood smear slides suitable for laboratory analysis. A drop of a blood sample aspirated from a sealed container is smeared onto a labeled microscope specimen slide and transported along a drying path to an outloader where the dried slide is placed in a compartmented multi-slide storage basket.

U.S. Pat. No. 5,766,549 issued Jun. 16, 1998, entitled "Apparatus for Drying Blood Smear Slides", discloses such an apparatus in which wet blood smeared on one surface of the slide is transported along the drying path with the wet surface facing upward. The downwardly facing opposite surface is exposed to a warm air flow so that the heat conducted through the slide minimizes distortions in the blood cell morphology. As the dried slide leaves the drying path an outloader deposits it into a compartmented storage basket. Prior art outloaders usually comprise a vacuum gripper which operates to grasp a slide via a vacuum force applied to the slide surface opposite the smear. The gripper initially grasps the slide when the slide is horizontally oriented. Thereafter, the gripper tilts the slide by 90 degrees, thereby vertically orienting the slide for positioning in the storage basket. While such prior art outloaders serve the basic transfer need, they can be problematic if small slivers of glass or the like disrupt the vacuum seal between the gripper and the slide surface. Should this occur, the slide can dislodge from the gripper, fall and break. Further, in such outloader devices, there is no provision for precisely registering a lateral edge of the slide so that it will always be properly located with respect to the storage basket.

SUMMARY OF THE INVENTION

It is therefore an object of the present invention to provide a novel and improved outloader which automatically grips a dried blood smeared slide for transfer from a dryer to a compartmented multi-slide storage basket.

Another object is to provide a slide outloader which transfers a microscope slide in rotation and linear motion from a horizontal plane at the exit of a dryer to a vertical plane for deposit in a slide storage basket by operation of a single stepper motor.

Still another object is to provide a microscope slide outloader capable of handling many sizes of slides.

A still further object is to provide a microscope slide outloader with four degrees of freedom of adjustment for precisely aligning the slide for deposit in a compartmented storage basket.

Briefly, these and other objects of the invention are accomplished by a microscope slide outloader in which a platen receives a slide in a horizontal or near horizontal orientation from a blood smear slide dryer and holds it firmly in place by a spring-biased gripper. A single stepper motor rotates the platen and slide to a vertical orientation and lowers both to a position where the slide is aligned with a compartmented multi-slide storage basket. A linear actuator then operates the gripper against the spring bias to release the slide for deposit into the basket. The platen is then returned to the upper position for receiving the next slide from the dryer. Preferably, the platen is slightly tilted (about 10 degrees) with respect to a horizontal plane when the platen is in its slide-receiving (upper) position so that a lateral edge of a received slide will be registered with a rectilinear edge on the platen.

For a better understanding of these and other objects and aspects of the invention, reference will be made to the following detailed description, taken in conjunction with the accompanying drawings wherein:

DESCRIPTION OF THE PREFERRED EMBODIMENT

Figure 1:
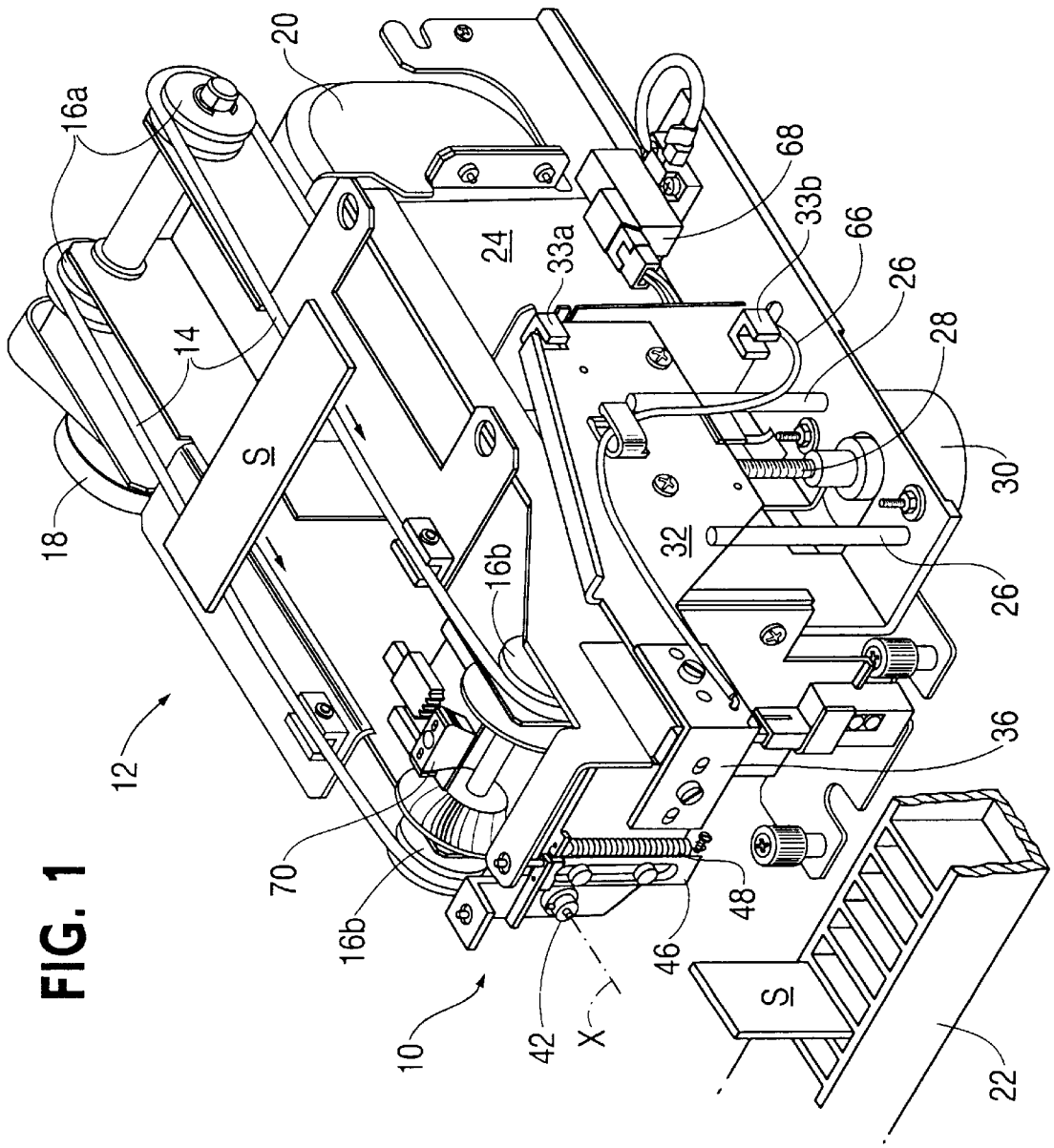
FIG. 1 is a perspective view of a dryer apparatus for an automatic blood smear slide maker incorporating a slide outloader according to the invention for transfer to a compartmented storage basket.
Figure 2:
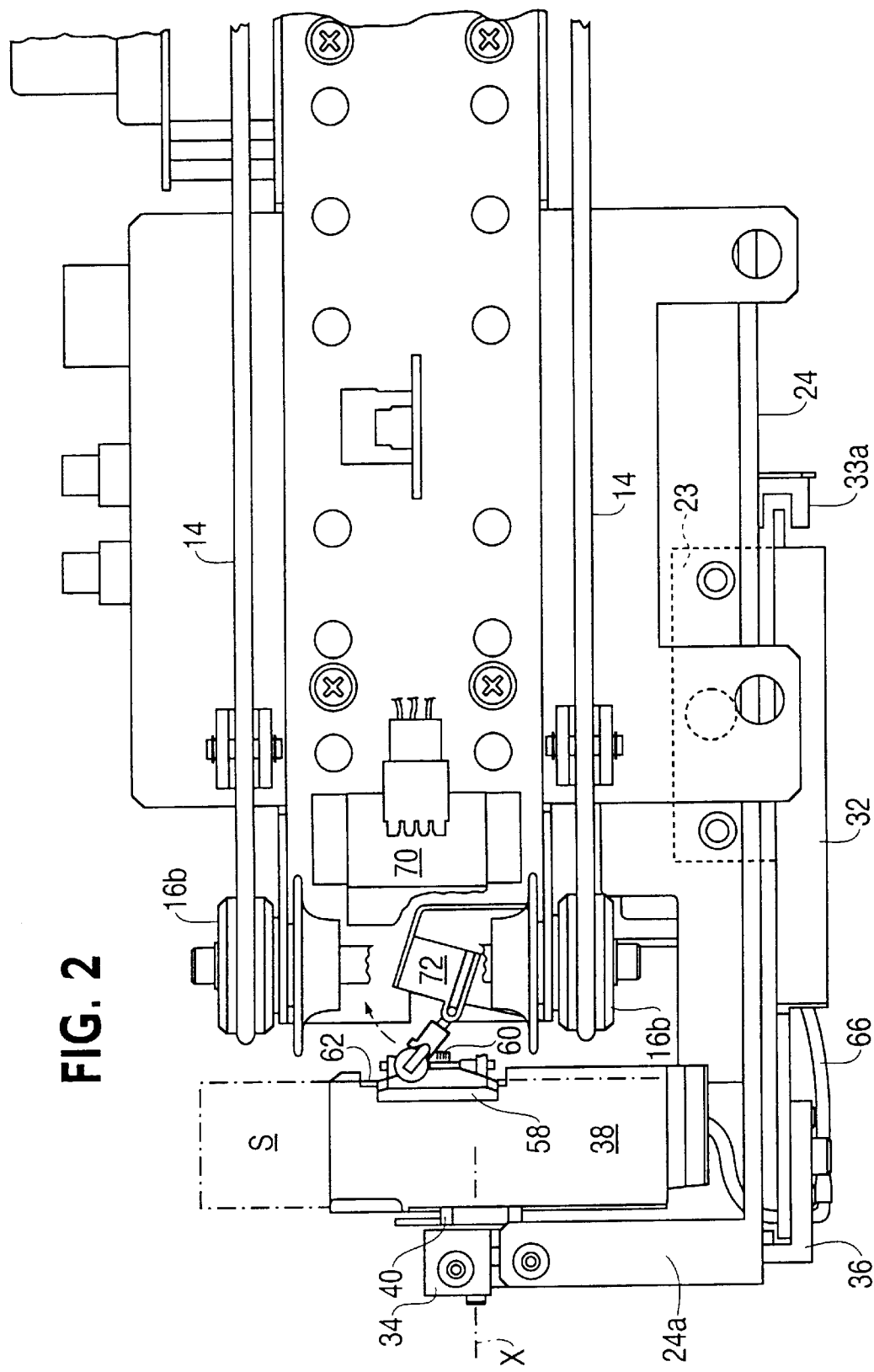
FIG. 2 represents a top view of the outloader and adjacent portions of the dryer of FIG. 1 with a slide shown in broken outline in a horizontal position of transfer.

Referring now to the drawings wherein like reference characters denote like or corresponding parts throughout the several views, FIG. 1 shows a slide outloader 10 according to the invention mounted on the exit end of an elongate blood smear slide dryer 12 such as disclosed in U.S. Pat. No. 5,766,549, supra.

Dryer 12 comprises a pair of parallel endless cords 14 on two inlet sheaves 16a synchronously driven by a stepper motor 18 and two exit sheaves 16b for slowly conveying wet blood smeared slides S (only one being shown) along a generally horizontal drying path. Cords 14 are preferably made of a polyurethane with a stick surface for frictionally holding slides S in place as they move along the drying path. Slides S are deposited lengthwise across cords 14 in timed sequence at the inlet end of dryer 12 with the dry sides facing downwardly in a horizontal plane. The dry sides are exposed to the warm air from a chamber 20 located beneath the path in order for heat conducted through the slide to dry the blood smear to minimize distortion of cell morphology in the blood smear. As each dried slide S reaches the dryer exit, it passes over exit sheaves 16b where it falls by gravity at a contact angle not exceeding 45 degrees measured from the top of sheaves 16b and lands on a platen 38 in a near horizontal position. As described hereinbelow, the platen may be adjusted as shown in broken outlining to approximately 10 degrees tilted from a horizontal plane. Thus as slide S falls onto the platen 38 from dryer 12, gravitational forces urge slide S in the lateral direction against registration wall 38a. The slide is then rotated by the outloader to a vertical plane for deposit in a compartmented multi-slide storage basket 22.

Figure 3:
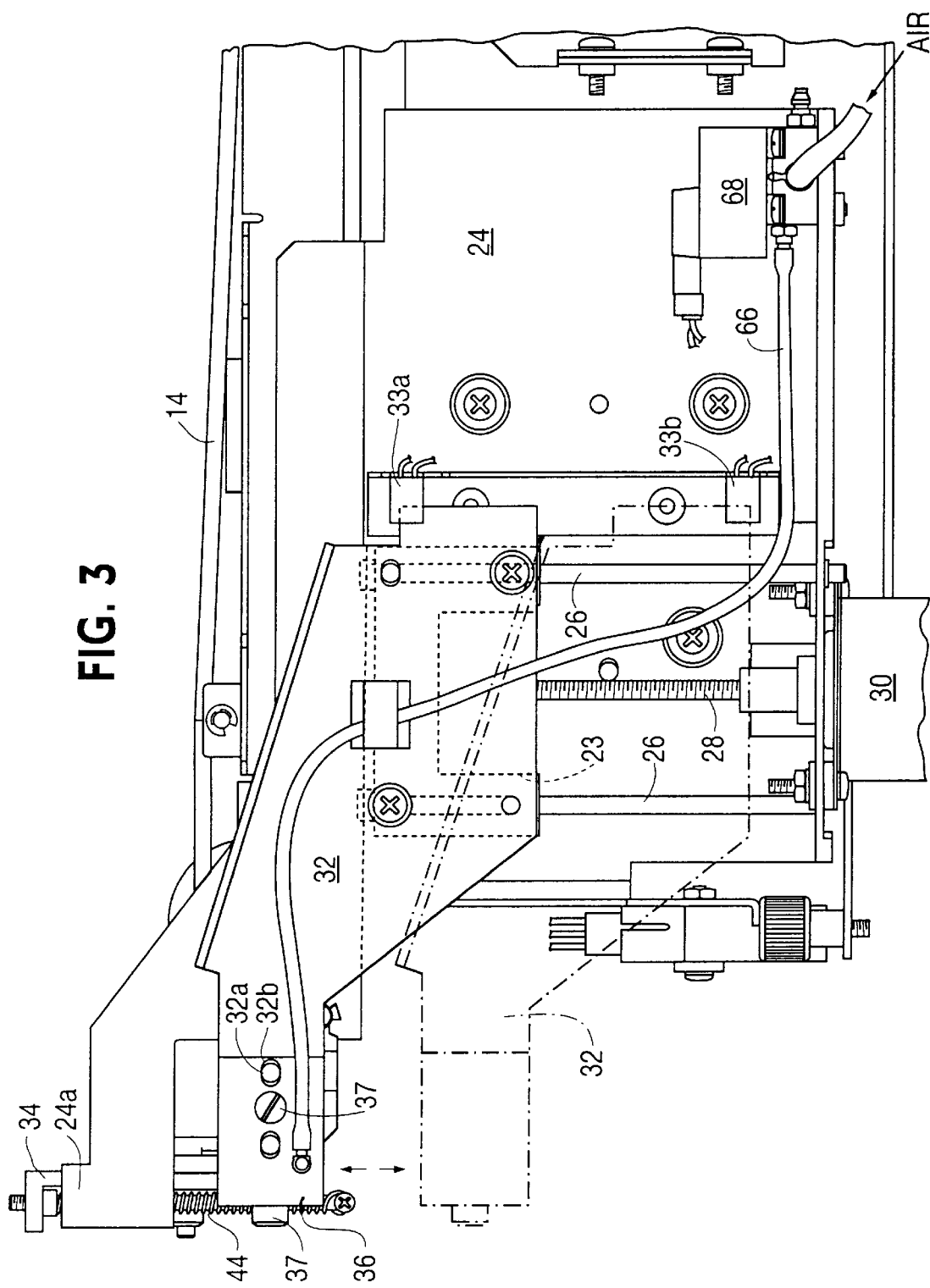
FIG. 3 represents one side of the outloader as viewed from the bottom margin of FIG. 2.

Outloader 10 includes a bracket 24 fixed to one side of warm air chamber 20 supporting a pair of vertical guide rails 26 on which opposite ends of a crossbar 23, shown in broken outline in FIG. 3, are slidable. A leadscrew 28 rotatably connected at one end to crossbar 23 and threadingly connected to a rotary stepper motor 30 at the other end causes an elevator 32, fixed to crossbar 23 by screws 32a, to move linearly in a vertical direction between upper and lower limits of travel as shown in solid and broken outline, respectively in FIG. 1. The upper and lower limits of travel of elevator 32 are determined by proximity sensors 33a and 33b which are electrically connected through limit switches (not shown) to motor 30.

An extension arm 34 connected by an adjuster angle 36 to elevator 32 supports a platen support arm 40 (FIG. 4) rotatable on a shaft 42 about an axis X parallel to the length of dryer 12, and spatially offset from the dryer exit at the upper limit of travel.

Figure 8:
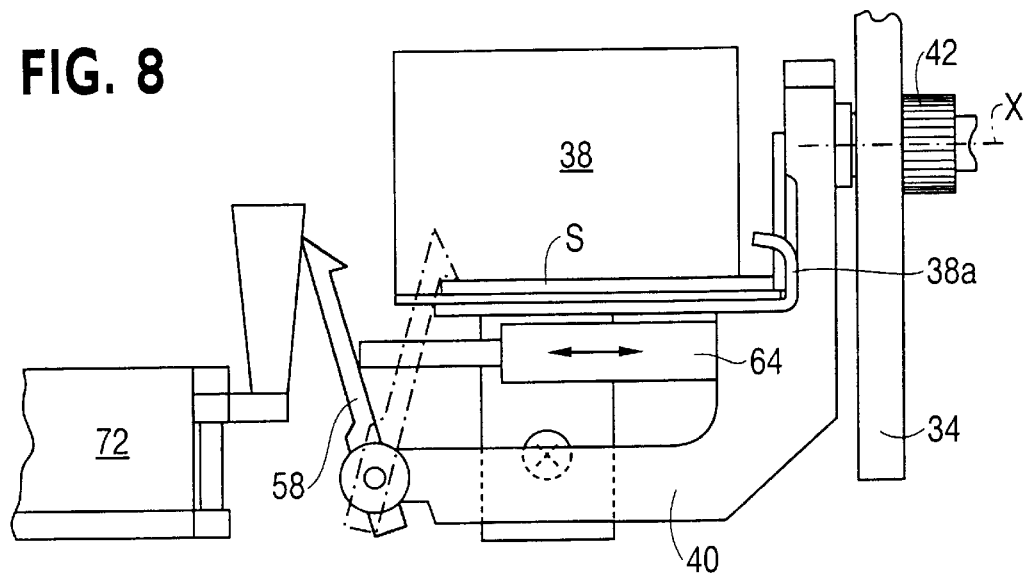
FIG. 8 is a more detailed side view of elements of the outloader positioned open for receiving the slide in the horizontal position of transfer.

As best seen in FIG. 8, an elongate platen 38 is secured to support arm 40 for receiving each slide S as it falls off the exit end of cord 14. Alignment of platen 38 for insertion in a compartment of storage basket 22 is linearly adjustable within limits determined by pairs of pins 32a and 34a extending respectively from arms 34 and elevator 32 and registering in horizontal slots 36a and 36b. Lockscrews 37 secure adjuster angle 36 to arm 34 and elevator 32 in the adjusted position.

Figure 5:
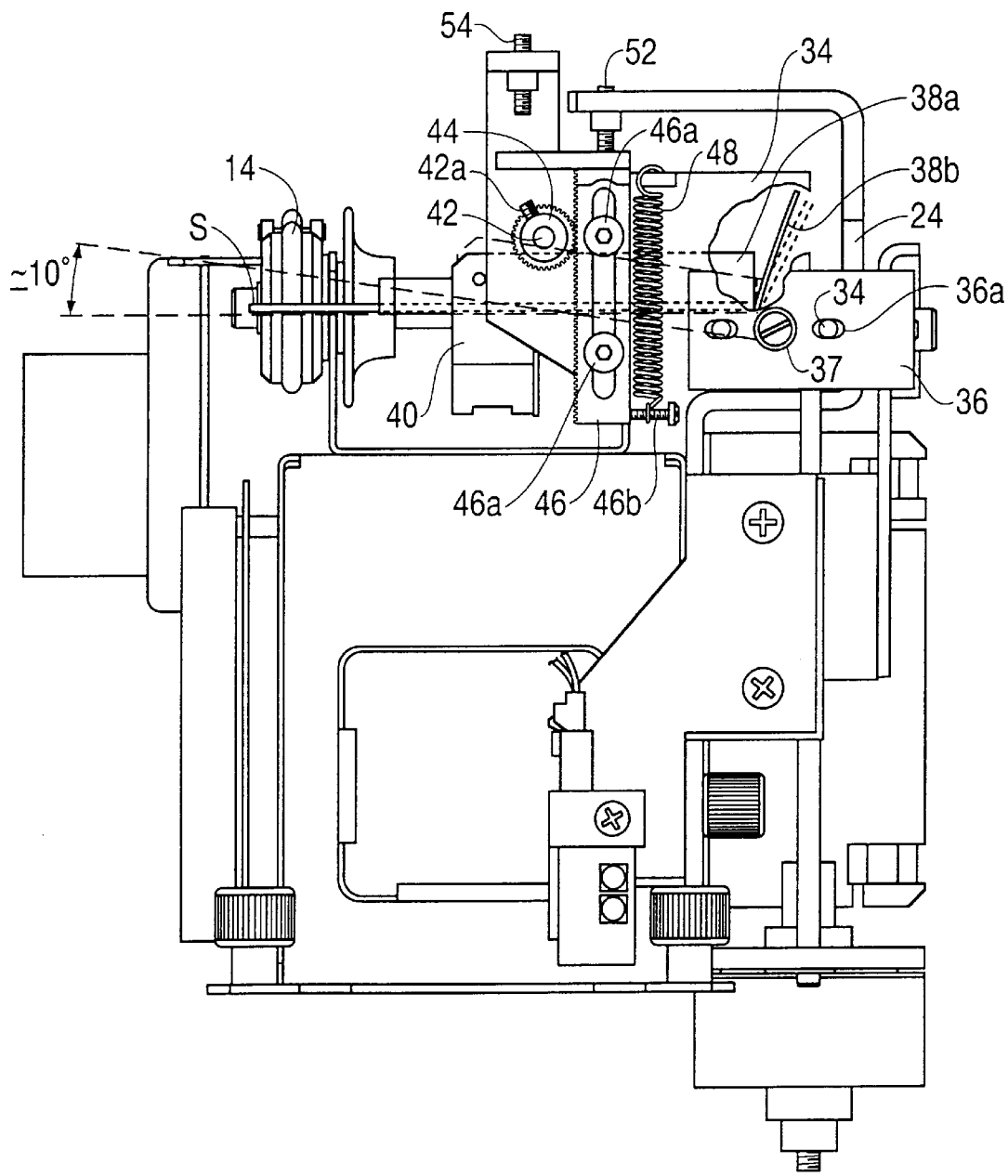
FIG. 5 represents the outloader as viewed from the left margin of FIG. 2, with the slide, shown partly in broken outline, gripped in a near horizontal position of transfer.
Figure 6:
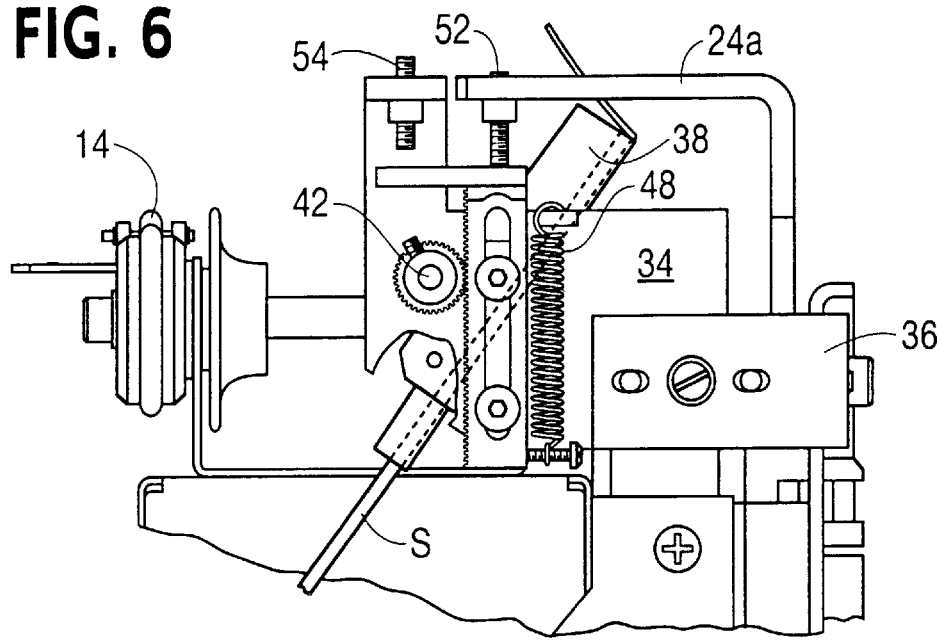
FIG. 6 represents the outloader of FIG. 2 with the slide, shown partly in broken outline, gripped in an intermediate position of transfer.
Figure 7:
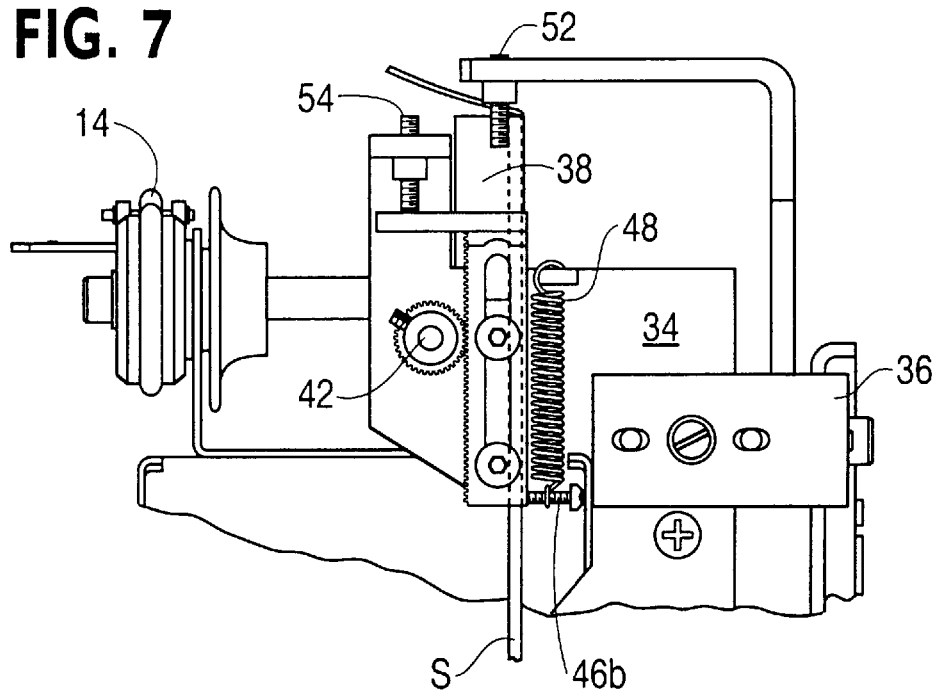
FIG. 7 represents a view like FIG. 6 with the slide, shown partly in broken outline, gripped in a vertical position of transfer.

Referring to FIGS. 5, 6 and 7, a rack-and-pinion mechanism comprising a pinion gear 44 fixed to rotatable shaft 42 by a set screw 42a rotates with platen support arm 40 and meshes with a vertically slidable, slotted rack 46. Spaced apart, vertically aligned guide pin 46a project from extension arm 34 and vertically slide within to rack 46. Setscrew 42a enables platen 38 to be aligned in the vertical position for deposit of slide S with a compartment of basket 22. A rack spring 48 connected between a lug 34a of arm 34 and an anchor screw 46b threaded into rack 46 urges rack 46 upwardly relative to arm 34.

A bracket arm 24a, extending horizontally from bracket 24 in spaced relation above rack 46, includes a vertically adjustable, mechanical stop 52 positioned to contact rack 46 a distance from the upper limit of travel sufficient for platen 38 to rotate 90-degrees from a horizontal position, or 110-degrees from the 10-degree tilted position, against the force of spring 48. As a result, platen 38 is rotated to the 10-degree tilted position when the upper limit is reached. As rack 46 begins to move downwardly from the upper limit, rack 46 is still engaged to stop 52 and the force of spring 48 rotates platen 38 back to the vertical position. Rack 46 then moves out of contact with stop 52 and contacts a vertically adjustable, mechanical stop 54 in extension arm 34 to maintain platen 38 in the vertical position as it continues to move toward the lower limit of travel.

Figure 4:
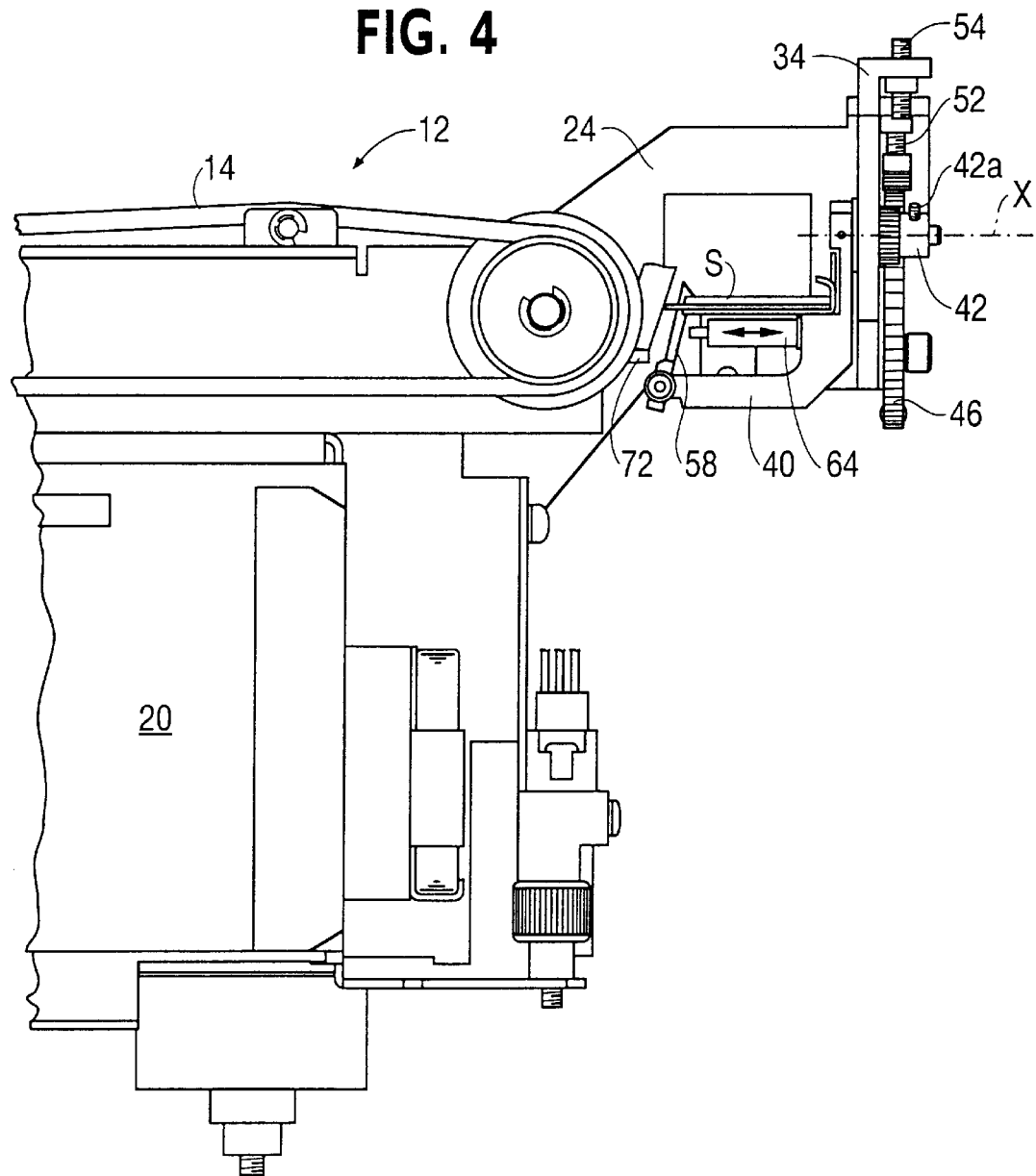
FIG. 4 represents the opposite side of the outloader as viewed from the top margin of FIG. 2 with the slide gripped in the horizontal position of transfer.

Referring to FIG. 4, a slide gripper 58 is pivotally connected to platen base 40 for gripping the slides during transport from a horizontal or tilted position to the vertical position. A torsion spring 60 urges gripper 58 toward a registration wall 38a along one edge of platen 38 distal from the exit end of dryer 12. A recessed edge 38b formed in platen 38 opposite from wall 38a is recessed an amount sufficient for gripper 58 to receive and capture slides, which are less than the unrecessed width of platen 38, against wall 38a.

Figure 9:
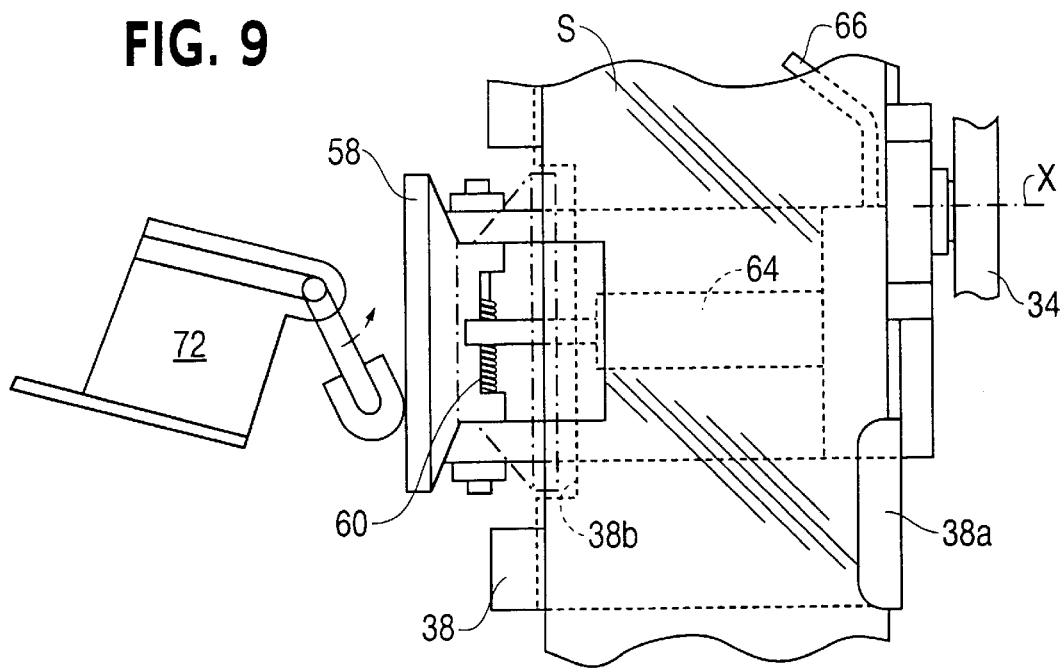
FIG. 9 represents a top view of the elements of FIG. 8.

As best seen in FIGS. 8 and 9, platen 38 with gripper 58 is shown in solid outline in an open position for receiving slides S, and in broken outline in a closed positioned for capturing the slide. A fluid actuated piston 64 mounted on platen base 40 opposes the force of spring 60 to open gripper 58. Fluid pressure for operating piston 64 is delivered through a conduit 66 by an electrically-operated, normally closed valve 68 whenever platen 38 is in the upper limit position for receiving a slide S from dryer 12, or in the vertical position at the lower limit of travel for dropping slide S into a compartment of basket 22.

An optical sensor switch 70 mounted on dryer 12 senses when a slide S approaches the exit of the dryer and signals valve 68 to operate piston 64 to push gripper 58 completely out of recess 38b for receiving the slide S. A gripper sensor 72 mounted on dryer 12 monitors the position of gripper 58 with a spring-biased, movable contact 72a extending from sensor 72 to ensure a slide is on platen 38. The position of sensor 72 relative to gripper 58 is adjusted so that contact 72a just touches the facing side of gripper 58 in the fully closed position with no slide on platen 38. When gripper 58 is fully closed, optical switch 70 is de-energized and sensor 72 is blocked, and when either fully open for receiving a slide or partially closed and holding a slide, gripper 58 moves contact 72a to unblock sensor 72. With a slide on platen 38, stepper motor 30 begins to move elevator 32 downward to a slide-releasing position causing spring 60 to rotate platen 38 to the vertical position.

A brief summary of operation of outloader 10 is as follows. Starting with platen 38 in the horizontal or 10-degree tilted position at the upper limit of travel of elevator 32, motor 30 is de-energized 30 and solenoid value 68 is energized to extend actuator 64 and hold gripper 58 in the open position ready to receive a slide S. When detector 70 senses a slide S approaching the exit of dryer 12 and enough time has elapsed for the slide to fall in place on platen 38, valve 68 closes to retract piston 64 and allow spring 48 and gripper 58 to capture slide S in platen 38. Gripper sensor 72 monitors the position of gripper 58 to ensure the slide is positively secured. If secured, sensor 72 energizes stepper motor 30 to move elevator 32 downwardly to a releasing position above basket 22. As it proceeds downward, spring 48 acting on stop 52 and rack 46 rotates pinion 44 an amount sufficient for platen 38 to attain a vertical position. Further rotation is prevented by rack 46 making contact with stop 54 as platen 38 continues downward to the lower limit of elevator 32. At the lower limit detector 33b stops motor 30 and extend piston 64 to open gripper 58 and release the slide. Sensor 72 confirms that platen 38 is empty and signals motor 30 to reverse direction and return platen 38 in reverse order of operation to the starting position. That is, as elevator 32 moves upward, rack 46 makes contact with stop 52 and begins rotation of platen 38 to the horizontal or tilted position at the upper limit position of travel of elevator 32.

Some of the many advantages and novel features of the invention should now be readily apparent. For instance, an automatic outloader is provided which is capable of transferring dried blood smeared slides of different sizes from a dryer to a compartmented multi-slide storage basket, which positively grips the slides on a platen for transfer in rotation and linear motion by a single stepper motor from a horizontal or tilted plane at the exit of the dryer to a vertical plane for deposit in the slide storage basket. The loader is adjustable in four degrees of freedom to insure precise alignment of the slides for deposit in the storage basket, is relatively simple in construction and operation, and occupies less space than outloaders of the prior art.

Various changes in the details, steps and arrangement of parts, which have been herein described and illustrated in order to explain the nature of the invention, may be made by those skilled in the art within the principle and scope of the invention as expressed in the appended claims.

What is claimed is:

1. An improved outloader for transferring blood smear slides from a dryer to a storage basket, the dryer including an elongate support frame with parallel endless cords for serially transporting the slides over a warm air plenum, the improvement comprising:

(a) an elevator moveable between an upper position at an exit of the dryer to a lower position at the storage basket;

(b) a platen pivotally connected to said elevator for receiving the slides discharged in a horizontal plane from the dryer in the upper position;

(c) means for rotating said platen at the upper position to vertical plane in the lower position;

(d) means pivotally connected to said platen for gripping a slide discharged from the dryer in the upper position;

(e) a spring operatively connected to said gripping means for holding and registering the slide on said platen; and (f) an actuator operatively connected between said gripping means in opposition to said spring for selectively releasing the slide in the lower position.

2. The improvement of claim 1 wherein said platen further comprises:

a wall along a first edge distal to the dryer when in the upper position for registering with the slides.

3. The improved outloader of claim 2 wherein said platen further comprises:

a recessed edge portion along a second edge of said platen proximal to the dryer and opposite from said wall, said portion being spaced from said wall a distance less than the width of the slides.

4. The improved outloader of claim 3 wherein said gripping means is positioned to register with said edge portion for pushing the slides against said wall.

5. The improved outloader of claim 4 wherein said actuator further comprises: a linear, fluid-actuated rod contacting said gripping means.

6. The improved outloader of claim 1 wherein said rotating means further comprises:

a pinion rotatably connected to said platen for rotation therewith;

a rack slidably connected in a vertical plane to said elevator and meshing with said pinion; and force-exerting means connected to said rack for urging said platen toward the horizontal position as said elevator moves to the upper position.

7. The improved outloader of claim 1 wherein said platen is adjusted, when in a slide-receiving position, to a near horizontal plane.

8. The improved outloader of claim 1 wherein said platen is tilted approximately 10 degrees with respect to the horizontal plane when said platen is in a slide-receiving position whereby a lateral edge of a received slide will register by gravitational force against a wall of said platen.

9. An improved outloader for transferring a specimen slide within a selected range of widths discharge from an end of a conveyor to a storage basket, the improvement comprising in combination:

an elongate platen having a width within the selected range;

an elevator vertically reciprocating said platen between a slide-receiving upper position across the conveyor end and a vertical lower position adjacent to the storage basket;

a rack-and-pinion means for rotating said platen between said position;

a wall along a first edge of said platen, distal to the conveyor end when in the upper position, for registering with a slide conveyed onto said platen;

a recessed edge along a portion of a second edge of said platen proximal to the conveyor when in the upper position end and opposite from said wall, said recessed edge being a distance from said wall at least the narrowest width of the slide within the selected range;

a gripper pivotally connected to said platen in juxtaposition to said portion on an axis parallel to the length of said platen for pushing the slide against said wall;

a spring means operatively connected to said platen for exerting a force to said gripper to hold the slide in registration against said wall; and an actuator operatively connected between said platen for exerting a force in opposition to the force of said spring for releasing the slide from said platen when in the lower position.

10. Apparatus for dispensing blood smear slides from a dryer into a storage basket, the dryer including an elongate support frame with parallel endless cords for serially transporting the slides over a warm air plenum to one end of the frame, the slides being arranged lengthwise across the cords, the apparatus comprising:

an elevator slidably connected to one side of the frame with a vertically moveable arm spaced from and athwart the one end;

a stepping motor mounted on said frame for vertically reciprocating said elevator between upper and lower limits;

a platen pivotally connected to said arm adjacent to the one end and having a planar surface for receiving the slides from the dryer;

a pinion rotatably connected to said platen for rotation therewith;

a rack slidably connected in a vertical plane to said arm and meshing with said pinion;

a spring connected between said rack and said arm for urging the surface of said platen into the vertical plane;

first rack adjusting means connected to said arm for setting said platen in a slide-receiving position at the upper limit of said elevator; and second rack adjusting means connected to said frame for setting said platen in a vertical position below an intermediate position of said elevator;

stop means connected to said frame for limiting the lower position of said arm;

a gripper means pivotally connected to one side of said platen adjacent to the discharge end spring-biased for capturing a slide dropped on said platen from the discharge end of the dryer; and actuator means operatively connected between said arm and said gripper means for pushing said retainer against the spring-bias to a slide-releasing position.

11. The apparatus of claim 10, wherein the slides are within a selected range of widths, further comprising:

a wall along a first edge of said platen distal to the dryer when at the upper limit of said elevator for registering with the slides.

12. The apparatus of claim 11 further comprising:

a recessed edge portion along a second edge of said platen proximal to the dryer and opposite from said wall, said wall being spaced from said wall a distance less than the width of the slides.

13. The apparatus of claim 12 wherein said gripper means is positioned to register with said edge portion for pushing the slides against said wall.

14. The apparatus of claim 10 further comprising:

sensor means for actuating said actuator means in response to the presence of a slide at the discharge end to push said gripper means against the spring bias to a release position.

15. The apparatus of claim 14 further comprising:

switch means secured to said frame for signaling the position of said gripper means.

16. An improved outloader for transferring blood smear slides discharged from one end of a dryer to a storage basket, the outloader including an elongate platen, an elevator for vertically moving the platen between an upper limit across the discharge end and a lower limit adjacent to the storage basket, the improvement comprising:

a rack-and-pinion mechanism for rotating the platen between a slide-receiving position at the upper limit and a vertical plane at the lower limit;

a wall along a first edge of the platen distal to the dryer discharge end for registering with a slide on the platen;

a recess along a second edge of the platen proximal to the discharge end oppositely disposed from said wall a distance less than the width of the platen;

a gripper rotatably connected to said platen adjacent to said recessed edge on an axis parallel to the length of the platen and formed to be inserted in said recess;

a spring operatively connected between said gripper and the platen for urging said gripper into said recess; and an actuator operatively connected between said gripper and the platen in opposition to the force of said spring.

* * * * *